(12) United States Patent
Baratta

(10) Patent No.: US 6,431,748 B1
(45) Date of Patent: *Aug. 13, 2002

(54) METHOD AND APPARATUS FOR THE NONDESTRUCTIVE DETERMINATION OF THE PURITY OF A TEST OBJECT

(76) Inventor: Francis I. Baratta, 13x Ridge St., Arlington, MA (US) 02474-1737

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 129 days.

(21) Appl. No.: 09/037,145

(22) Filed: Mar. 9, 1998

(51) Int. Cl.⁷ .............................................. G01N 25/00

(52) U.S. Cl. ............................................. 374/45; 374/5

(58) Field of Search ............................. 374/5, 45, 130, 374/12, 4

(56) References Cited

U.S. PATENT DOCUMENTS

| | | | | |
|---|---|---|---|---|
| 2,264,968 A | * | 12/1941 | De Forest | 374/7 |
| 2,342,029 A | * | 2/1944 | Zubko | 324/451 |
| 3,222,917 A | * | 12/1965 | Roth | 374/5 |
| 3,433,052 A | * | 3/1969 | Maley | 374/5 |
| 3,611,786 A | * | 10/1971 | Schorr | 374/44 |
| 3,672,204 A | * | 6/1972 | Green | 374/43 |
| 3,747,755 A | | 7/1973 | Senturia et al. | |
| 3,795,133 A | * | 3/1974 | Fergason et al. | 374/7 |
| 3,808,439 A | * | 4/1974 | Renius | 374/4 |
| 3,981,175 A | | 9/1976 | Hammond, III et al. | |
| 4,255,962 A | | 3/1981 | Ashman | |
| 4,381,154 A | | 4/1983 | Hammond, III | |
| 4,385,843 A | | 5/1983 | Hammond, III | |
| 4,630,938 A | * | 12/1986 | Piorkowska-Palczewska et al. | 374/44 |
| 4,799,999 A | | 1/1989 | Medvinsky et al. | |
| 5,005,985 A | * | 4/1991 | Piorkowska-Galeska et al. | 374/44 |
| 5,052,819 A | | 10/1991 | Baratta | |
| 5,080,766 A | | 1/1992 | Moment et al. | |
| 5,128,016 A | | 7/1992 | Moment et al. | |
| 5,131,758 A | * | 7/1992 | Heyman et al. | 374/5 |
| 5,218,303 A | | 6/1993 | Medvinsky | |
| 5,667,300 A | * | 9/1997 | Mandelis et al. | 374/43 |
| 6,095,680 A | * | 8/2000 | Baratta | 374/43 |

OTHER PUBLICATIONS

M. Clayton, The Collectors Dictionary of the Silver and Gold of Great Britian and North America, 1971, pp. 15–16, The World Pub. Co. New York & Cleveland.

ASTM Test Method B562–95, Standard Specification for Refined Gold, 1995, pp. 385–387, Amer. Suc. for Testing & Matls, Philadelphia, PA.

ASTM Test Method B413–89, "Standard Specfication for Refined Silver," 1989, pp. 244–245, ASTM, Philadelphia, PA.

(List continued on next page.)

Primary Examiner—Diego Gutierrez
Assistant Examiner—Stanley J. Pruchnic

(57) ABSTRACT

This invention will provide a method of determining nondestructively, the purity or composition of an unknown material sample, such as, for example a sample of gold or silver of unknown purity. Their forms can be a: casting, bullion, coupon or disc (a coin), as well as some jewelry, such as gold or silver rings with signet surfaces. The test specimens are such that their areal dimensions are large compared to their thicknesses, thus qualifying as 'slabs'. In order to detect a particular adulterant the method may require a dual-test procedure: The first is an application of a pulse of constant heat (or cold) and the second, if necessary, is an application of constant temperature. Furthermore, during the time the conditions are applied the slopes of the time-varying temperature patterns can be determined, the decay curves, after such conditions are removed, and their slopes can also be realized. Such information will provide a further check on the authenticity of the test item.

20 Claims, 5 Drawing Sheets

OTHER PUBLICATIONS

ASTM Test Method E 378–83, "Standard Tes Method for Spectrographic Analysis of Silver by the Power Technique," pp. 54–56, ASTM, Philadelphia, PA.

ASTM Test Method E 1446–92, "Standard Test Method for Chemical Analysis of Refined Gold By Direct current Plasma Emission Spectroscopy," 1992, ASTM, Philadelphia, PA pp. 431–433.

Carblaw & Jaeger, *Conduction of Heat in Solids*, 1947, pp. 85, 97 & 251, Oxford Clarendon Press, Amen House, London, England.

J.M. Looney, Jr., & F. Pompei, "Ear Thermometry," Medical Electronics, 1989.

A.B. Newman & L. Green, "The Temperature History abd Rate of Heat Loss of an Electrically Heated Slab," Trans. of the Electrochemical Soc., 1934, vol. 66, pp. 345–347, USA.

W.H. McAdams, *Heat Transmission* 1954, 3rd Ed. McGraw–Hill Book Co., Inc, NY, Toronto, London, pp. 460–461.

* cited by examiner

METHOD AND APPARATUS FOR THE NONDESTRUCTIVE DETERMINATION OF THE PURITY OF A TEST OBJECT

FIELD OF THE INVENTION

The present invention relates to the nondestructive determination of the composition of a material when comparing the thermal properties of a sample of the material with the thermal properties of a standard of a similar material, said standard or substitute having a desired composition.

The invention herein described has use for nondestructive qualitative determination of composition of a variety of materials and its use is discussed mostly with reference to precious metals, such as gold and silver.

BACKGROUND OF THE INVENTION AND PRIOR ART

Background

The rise in trading in recent years of precious metals, such as gold and silver, as commodities, and the rise in their unit prices has increased the need for an economical, fail-safe mechanism for determining nondestructively, the purity of such materials. Since gold, like silver, is often transferred or sold by persons not particularly knowledgeable about such precious metals to one of greater knowledge, it is important that some way be found to detect forgeries and ascertain the purity of such precious metals that avoids the costly and time consuming methods, several of which are outlined below, a way that is nondestructive, fast and accurate.

By way of background, that which follows was paraphrased from *The collector's Dictionary of the Silver and Gold of Great Britain and North America*, Michael Clayton, World Publishing Company, 1971.

Pure gold is extremely heavy in proportion to its volume and also very soft (malleable), and if pure, is referred to as '24 carat'. Silver is not so malleable and only approximately half the weight of a piece of gold of similar volume. Both are too soft to use in their pure form and must be hardened by the admixture of base metals, usually copper, though silver may be used with gold. If both silver and copper are added to gold it becomes pale and green in color. The fact that adding a 50 percent alloy of copper to silver retains a silvery appearance can easily lead to fraud without protection. In general, the best proportions of gold and alloy are 22 parts pure gold to 2 parts alloy, but this can be varied so that 18, 15, 12, or 9 carats (or parts) are balanced by an alloy making up 24 parts. These balanced fractions of pure gold and alloys are legally used and obviously the less pure gold parts, the cheaper the finished product. With silver, only two standards are permitted in Great Britain, 925 parts out of 1000 as normal Sterling standard and 958.3 parts as the higher Britannia standard. By the same measurement, 18 carat gold is the equivalent of 750 parts fine gold to 1000 (24 carats). For most of the English gold coinage and all since 1672, the fineness has never been below 22 carats (916.66 parts gold to the 1000). Since the nineteenth century in the United States, the coin standard is 900 parts pure silver to 100 parts alloy.

In order to protect the buyer of gold and silver, a system of testing, or assaying, and checking the quality and standards of an object is necessary. This can be done by comparison (touch), weight, or chemical means. The first demands considerable visual skill as the object to be tested and a piece of known quality are both stroked across a piece of basanite, a hard flint-like slate, and the resulting streaks compared. In the second test, weight, small portions of the object to be assayed are scraped from each piece, wrapped in lead (lead and silver are also used to wrap gold) and heated in a bone-ash crucible. As the heat is applied lead and other base metals oxidize and are absorbed by the crucible, known as a 'cupel'; the balance is then weighed and compared with the weight of the original scrapings.

In the case of gold, which is also wrapped in silver, a further process is required whereby the silver is finally removed by placing it in hot nitric acid. This method was first recorded in 1495. If on completion of these tests, the gold or the silver are found to be below the lowest permitted standards, the marks which would guarantee their quality, 'hall-marks', as they are known, are withheld and the objects under examination are crushed and returned to the maker. The third is a simple method and applicable only to silver, but requires some reasonable idea of the quality of the metal being tested. This involves the dissolving of the weighed scrapings, also known as 'diet', in nitric acid and the addition of a standard solution of sodium chloride (common salt); at a certain point the cloudy liquid clears and silver chloride is precipitated. A comparison of the original weight of the silver sample and the quantity of saline solution required to do this enables the fineness of the metal to be assessed.

Historically, as indicated above there are a number of methods used to determine the composition of metallic materials that can be classified as comparative as well as destructive. A comparative method is one, as the name implies, that requires a comparison to a known reference material. A destructive test is as the name implies and needs no explanation. The descriptions of pertinent testing methods that follows are all comparative tests and are categorized as 'destructive' or 'nondestructive'. The following paragraphs, under the heading "Prior Art", discuss appropriate examples of these.

Prior Art

Destructive Tests

Some of the more modem methods, than those described above, that have been developed and in use today to determine alloy content of metallic materials are: optical emission spectrography, spectrometry, x-ray fluorescence spectrometry, atomic absorption spectrometry, plasma emission spectrometry and combustometric analysis to determine particular elements. Such methods are not only costly, but usually require a sample from the test piece, and thus are somewhat destructive.

A primary example of a destructive test is the standard prescribed by the American Society for Testing and Materials, (ASTM) Test Method B 562-95, "Standard Specification for Refined Gold". This test method examines samples taken from the melt before pouring the casting of gold. The standard utilizes, for 99.5 percent purity, a test method for chemical analysis by cupellation fire assay. If there is a disagreement between the manufacturer and the purchaser the specified test will then be in accordance with ASTM Test Method E 1446, "Test method for Chemical Analysis of Refined Gold by Direct Current Plasma Emission Spectroscopy".

The standard for testing silver, which is also destructive, is that given by the ASTM Test Method B 413-89, "Standard Specification for Refined Silver". This method requires that the samples be taken from bars by drilling six holes and the chemical composition is determined in accordance with ASTM Test Method E 378 "Test Method for Spectrographic Analysis of Silver by the Powder Technique".

Portable electronic gold testers that measure the carat value of gold are also available, such as those described in U.S. Pat. Nos. 4,799,999 and 5,218,303, authored by Medvinsky and Radomyshelsky. These patents describe a method for determining the assay of gold alloy, utilizing an electrochemical process. The specimen gold is wetted by an electrolyte, and a small current anodizes the surface of the specimen for a metered period of time. A potential sensing device is then applied to the charged surface, and a potential decay is observed. The potential decay information is compared with empirical data and by interpolating the potential with the empirical data a determination of the carat quality of the gold alloy may be determined. This same method may be used for other precious metals, employing different electrolytes, empirical standards, and potentiometers.

There are two additional patents, U.S. Pat. Nos. 5,128,016 and 5,080,766, authored by Moment and Nelson, that essentially utilize the same technique with some variation as those indicated above.

Criticisms of these gold testing devices are that they are slightly destructive, are surface sensitive only, will not detect plating or gold overlay, and will leave a mark on items that are of 14 carat or less.

Nondestructive Tests

There are several methods of nondestructively discriminating between bodies having similar appearances but of slightly different composition or even of different material. In one instance the relatively old technique of eddy current testing is utilized to attempt to separate higher grade from lower grade materials. This method principally compares the subsurface electrical conductivity, synonymous with thermal conductivity, and magnetic permeability of a resulting read-out waveform of the higher grade standard material to that of the sample. The conductivity of gold and a mixture of gold with an adulterant will be very similar, as will silver and a mixture of silver with an adulterant, and thus the sensitivity of the eddy current technique will not be sufficient to separate such forgeries. Also, if a tungsten body, which has the same density as gold, is gold plated at a surface depth deeper than the subsurface penetration of the eddy current, then this test method will not discriminate between pure gold and the forgery.

In another instance U.S. Pat. No. 4,255,962, issued to Ashman, teaches a method of distinguishing a simulated diamond from a natural diamond by utilizing a probe which applies a pulse of heat to the surface of the sample in an air environment and during the occurrence of thermal equilibrium the same probe detects the change in temperature. This change in temperature is related to the thermal conductivity of the sample. Since the thermal conductivity of natural diamond is at least an order of magnitude greater than a simulated diamond, such as cubic zirconia, it is readily detected. This method, however, is not sensitive enough to detect the slight change in thermal conductivity between pure gold and a forgery or pure silver and a forgery.

Another example of a nondestructive test method is described in U.S. Pat. No. 3,981,175, which was issued to Hammond, III and Baratta. In accordance with that patent, the device is a nondestructive counterfeit gold bar and silver bar detection system based upon heat transfer principles. Regarding the testing of gold the principle entails the application of identical finite suddenly applied controlled heat pulses at a first region which is one end of an elongated gold bar of specific dimensions and of known purity, used as a standard, and a geometrically identical test bar. The system is completely enclosed in an insulating medium. The temperatures, which are measured at a second region at the far end of each bar are not only dependent upon the thermal properties of each bar, but upon its length and the length of the test time. Those thermal properties, which in gold are unique, are specific heat, thermal conductivity and density; the combination of these properties is defined as thermal diffusivity. Since these properties in gold are singular, the temperature at the second region, i.e., the end opposite from that which is suddenly pulsed by a quantity of heat, will usually be at a higher temperature in a given time than that of a bar of a particular length less pure than the standard gold bar of the same length. Because of the large differences in thermal properties of gold and an alloyed gold sample, temperature measurements conducted at the far end will reveal differences.

The general heat transfer equation for the aforementioned situation is given in the following:

If heat (e.g., a square wave pulse of indefinite duration) is applied to one end of a gold bar, at x=L, the general equation given in U.S. Pat. No. 3,981,175 for the temperature T(x,t) at any distance x along the bar's length is:

$$T(x,t)=QL/k\{\alpha t/L^2+(3x^2-L^2)/6L^2-2/\pi^2\Sigma_{m=1}^{\infty}(-1)^m/m^2[\exp(-\alpha m^2\pi^2 t/L^2)]\cos(m\pi x/L)\} \tag{1}$$

Where: Q is the suddenly applied constant heat flux applied over an area (BTU/sec-ft$^2$) of the bar, at x=L, L is length in feet, k is the thermal conductivity (BTU/sec-ft-F), $\alpha$=k/$\rho$c, which is the thermal diffusivity in ft$^2$/sec, c is the specific heat (BTU/lb-F), $\rho$ is the density in lbs/ft$^3$, t is time in seconds, x is the distance in feet along the length of the sample and T(x,t) is temperature in degrees F. Note at x =0, at the far end there is no flow of heat because of the insulation, See Carslaw and Jaeger *Conduction of Heat in Solids*, Oxford Press, 1950.

The nondestructive testing of silver bars described in U.S. Pat. No. 3,981,175 is essentially the same as that indicated above except rather than employing a pulse of heat a constant temperature source is applied. Silver has the highest thermal diffusivity of any known material and the equation for the temperature along the bar length is dependent upon thermal diffusivity. Therefore, as a function of time, the silver bar will attain a higher far end temperature than any other material. The equation for the temperature at the far end is given in the following:

$$T(t)=2T_0\Sigma_{n=0}^{\infty}(-1)^n\{1-erf[(2n+1)/2(\alpha t/L^2)^{1/2}]\} \tag{2}$$

Where $T_0$ is the applied constant temperature above ambient and 'erf' is the standard definition of the error function; well tabulated in many references.

The method of U.S. Pat. No. 3,981,175 requires that the standard and test sample be completely insulated and the further restrictions are that: The standard and test sample must be elongated bars of the same particular length, and temperatures at the far end of each bar must be taken over same particular time interval after the heat is applied, depending on the length of the bar.

Yet another example of a nondestructive test method to detect fraudulent precious metal bars is revealed in U.S. Pat. No. 4,381,154, issued to Hammond, III. It was found that of all possible forgeries, a non-alloyed tungsten forgery of gold, i.e., an insert of tungsten within the gold bar, is the most difficult to detect because the density and heat-capacity of tungsten and gold are virtually identical (a less difficult forgery to detect is an alloyed forgery wherein its composition is generally uniform throughout). Thus, an improvement in accuracy over the previous U.S. Pat. No. 3,981,175 was required at that time. This improvement consists mainly of increasing the accuracy of the detection system by providing and controlling heat into the test chamber resulting in equilibrium, termed "dynamic insulation" by the author; accurate heater control and using a compensated infrared sensor to measure the temperature at the far end opposite the heated end of the sample. Also the author claimed that this method allowed the determination of the density, thermal conductivity and heat capacity of a given material.

Although the improved techniques adopted in U.S. Pat. No. 4,381,154 will enhance the sensitivity of this test method, it still requires that the test piece be an elongated bar of specific dimensions and additional temperature sensors, controls and electronic instrumentation compared to the method of prescribed in U.S. Pat. No. 3,981,175. It is also noted that the present day infrared temperature sensors can readily determine temperatures to an accuracy within 0.10 C. over a wide range of temperatures (see the paper by J. M. Looney, JR., and F. Pompei, Medical Electronics, 1989), thus superseding the method proposed in U.S. Pat. No. 4,381,154.

An additional improvement is described in U.S. Pat. No. 4,385,843 granted to Hammond, III, whereby an induction heater is employed to provide a pulse of heat to a bar of precious metal to determine if it has the purity of composition within a given range of variance. Heat is induced at one end of the bar using an induction heater powered by a high frequency power source, and the time versus temperature response at the other end of the bar is monitored. This device was employed, according to the author, to circumvent the problems associated with contact heaters. However, present day lasers or infrared heat sources will accomplish the same goal.

A more recent U.S. Pat. No. 5,052,819, was issued to Baratta; this document taught a method of nondestructively identifying materials and fraudulent carbon steel fasteners. This invention compared the characteristic temperature-time curve of a standard fastener to a test fastener by simultaneously providing a pulse of heat to both fasteners and measuring the temperatures at their heated ends. However this patent required an insulated receptacle and specified that the standard and test sample be restricted to elongated bars.

SUMMARY

The device will provide, broadly, a method of determining nondestructively, the purity or composition of an unknown material sample, such as, for example a sample of gold or silver of unknown purity. The form of the sample can be a casting, a bullion, a coupon or a disc (a coin) or even gold or silver rings with partially flat surfaces, such as signets. The uniqueness of the invention involves first subjecting one of the large surfaces of the sample of known thickness to a constant energy heat pulse or a constant cold pulse relative to the initial temperature of the sample and comparing the time-varying temperature pattern at the same surface thereof, or at the opposite surface during finite lengths of time with that of a known and identically-sized standard subjected to the equivalent conditions for an interval of time of the same finite length. The temperature of said surface or the opposite surface can be monitored during the time the heat or cold pulse is applied and/or after withdrawal. The second test, if needed, is in the form of the application of constant temperature and will eliminate an adulterated gold item that may not have been detected by the first test; this is referred to as a dual test method. In addition, the slopes of the time-varying temperature patterns during the time the condition is applied and/or after it is withdrawn can also be determined.

Improvements over the present state-of-the art consist of eliminating the need for a specified sample shape such as an elongated bar of a particular length, as well as a completely insulated environment and allowing testing of samples whose surfaces are exposed to a medium, and the use of both contacting and non-contacting heating units; and noncontacting temperature sensing elements. Further improvements are realized by examining: the slope of the temperature-time curves, the decay of the temperature-time curves after the heat or cold pulse, or constant temperature is removed, as well as the slope of the decay curve. These improvements are applicable to field operations.

BRIEF DESCRIPTION OF THE DRAWINGS

Other and further objects, advantages and features of the invention will be apparent to those skilled in the art from the following description thereof, taken in connection with accompanying drawings, in which.

DESCRIPTION OF THE PREFERRED EMBODIMENTS

In the description of the preferred embodiments that now follows, the invention is first discussed with reference to a system for determining nondestructively the composition of an unknown sample in various forms and, to simplify the explanation, the samples taken up are precious metals, gold and silver, but it will be kept in mind that most aspects of the system discussed with respect to such materials may also apply to other materials not having unique thermal properties as those of gold or silver.

It is noted that in the descriptions that follow where reference is made to the application or discontinuance of heat to the various bodies, it is understood to be equally applicable to cryogenic operations as well, which can be accomplished, for example, by the application of chilled objects of defined sizes or with liquids or liquefied gases in contact with the sample and the standard for comparison. However, this is not repeated in each case for the sake of brevity.

As previously mentioned in the discussion of U.S. Pat. No. 3,981,175 in the prior art, the shapes of the standard and the sample were required to be in the form of elongated bars of specific dimensions where both were insulated. The formulation in the aforementioned patent is given by Carslaw and Jaeger supra. These authors, as well as A. B. Newman and L. Green in their paper entitled "The Temperature History and Rate of Heat loss of an Electrically Heated Slab," in Transactions of the Electrochemical Society, Vol. LXVI, 1934, also indicate that if the four edges of a slab are large compared to their thickness, then heat flow toward the edges may be neglected. Therefore, if these dimensions are so large compared to the thickness, such as bullion, coupons and discs (coins), and most importantly, these cases can be considered from the view of thermodynamic analysis as approaching slabs, then the general aforementioned heat transfer equations, equations (1) and (2), can also be applied to the bodies of interest here, e.g., bullion, coupons, discs (coins), including certain shapes of jewelry, which will be discussed later.

Figure 1:
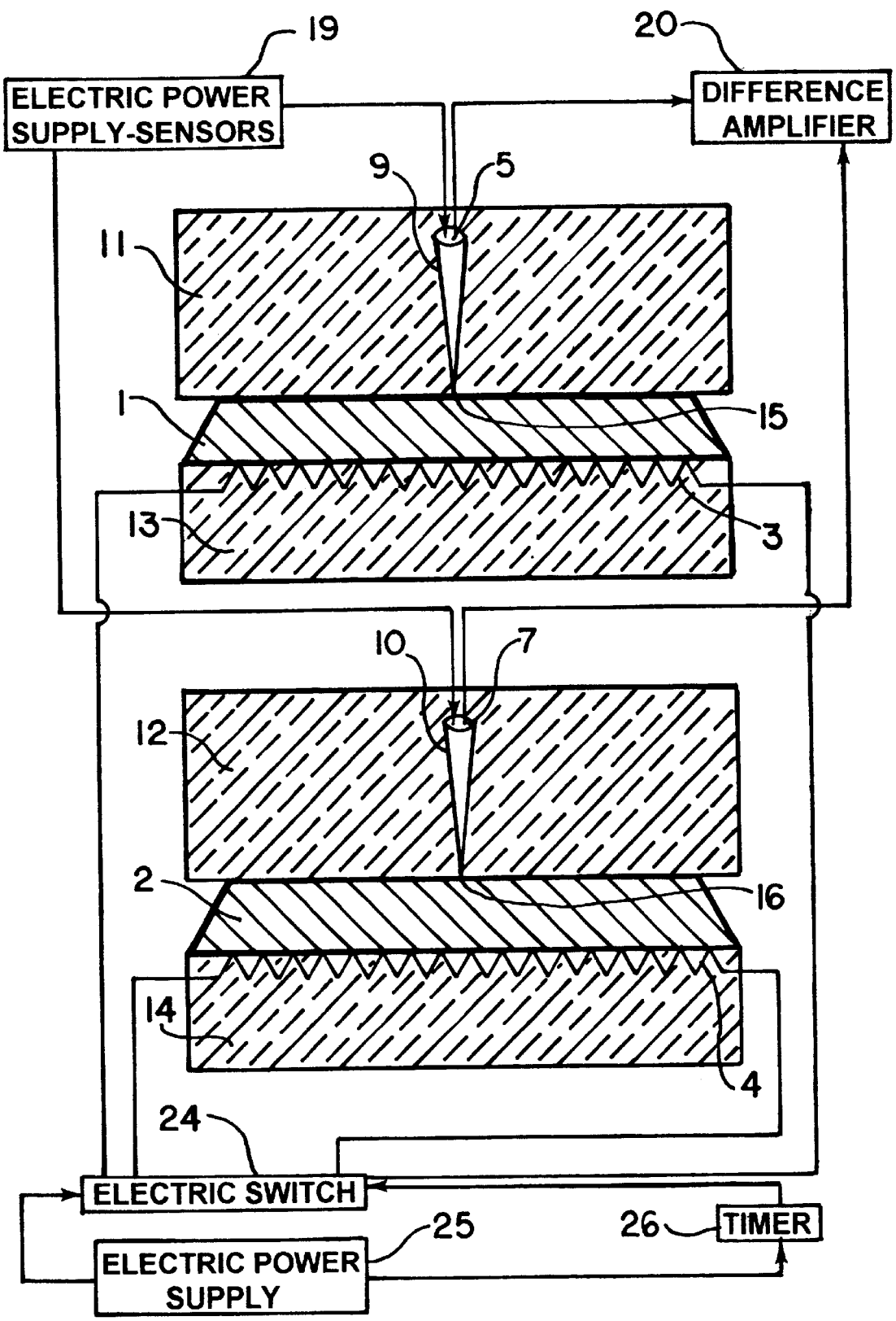
FIG. 1 is a diagrammatic representation, partly block diagram in form and the portions of the apparatus shown being partly cut away, of a system adapted to effect nondestructive determination of the composition of a material sample in the form of bullion, a coupon, or a disc.

Turning now to FIG. 1, which is a partly cut-away schematic of the apparatus for such nondestructive determination of gold bullion, a coupon, or a coin sample. Gold bullion, including gold coupons, have large width and length dimensions and gold coins have large diameters compared to their thickness. To qualify as a 'slab' the ratio of the edge dimensions, i.e., length, width or diameter, to the thickness can be approximately 3/1 or greater. Sample 1 of unknown composition, is compared to a standard gold bullion, coupon or coin 2 of known composition. Although in FIG. 1 and subsequent figures, the sample and standard are shown as bullion, it is understood that the concepts as now explained are equally applicable to castings, coupons, discs (coins) and in some instances jewelry. An electric-resistance heater 3, making contact over the full bottom surface of sample 1, which is insulated from the environment by insulation 13, applies a sudden pulse of constant energy and at the same time an identical electric-resistance heater 4, which is insulated from the environment by insulation 14, applies a sudden pulse of constant energy over the full bottom surface of the standard 2, thereby providing the same time-varying temperature patterns in the sample and the standard. Simultaneously, with or at a predetermined time after the heat is applied and for a predetermined time interval, or after the heat has been shut off and for a predetermined time interval, the temperature or time-varying temperature patterns of the sample, and the standard are sensed or noted and compared. The sensing functions are provided by infrared temperature sensor 9 focused on a spot 15 located at the middle of the top surface of sample 1 by a focal lens 5 and an infrared temperature sensor 10 located at the middle of the top surface of standard 2 focused on a spot 16 by a focal lens 7, both operatively disposed to sense the time-varying temperatures of the sample and the standard, thus providing as output an electrical signal that is a function of the time-varying temperature. Rather than utilize contacting temperature sensors as in U.S. Pat. No. 3,981,175, non-contacting infrared temperature sensors 9 and 10 are employed; a further improvement.

The top surface of sample 1 is insulated from the environment by insulation 11, which also encloses temperature sensor 9 and focal lens 5. Also, the upper surface of the standard 2 is insulated from the environment by insulation 12, which also encloses temperature sensor 10 and focal lens 7. As previously explained, the edges of the sample and the standard need not be insulated because they behave thermodynamically as heated slabs; this is an important embodiment. Each pair of heating means, as well as the sample 1 and standard 2 are well distanced from each other so as to eliminate thermodynamic interference between the two systems. The two electrical signals are connected as inputs to a difference amplifier 20 that notes any difference between the two electrical signals due to a temperature differential and amplifies the same.

Figure 2:
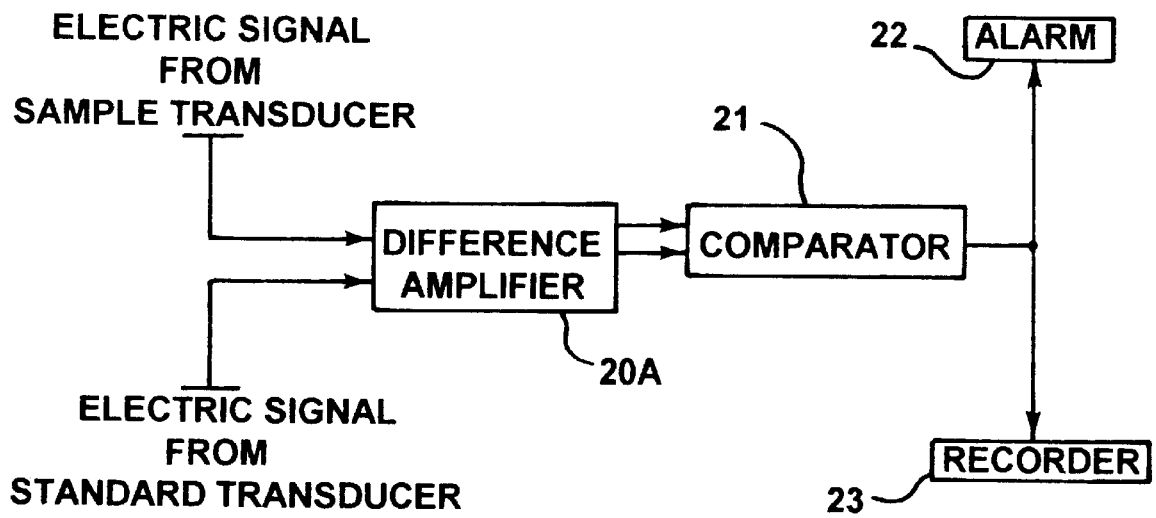
FIG. 2 shows in block diagram form a part of the system of FIG. 1, but slightly modified.

In FIG. 2, a comparator 21 is connected to receive an output from the difference amplifier 20A and is connected to an alarm 22 which is activated in those instances when the content of sample 1 varies from that of the standard 2, or to a recorder 23. As FIG. 1 shows, and to complete the electric circuitry of FIG. 1 by which sample purity is evaluated or analyzed, the heaters 3 and 4 are electrically energized through a switch 24 from an electrical power supply 25. The sequencing and timing of the events in the system are provided by a timer means 26.

In the apparatus shown by FIG. 1, the heating elements 3 and 4 are in contact with the bottom of sample 1 and sample 2, respectively, and temperature sensors 9 and 10 are focused on the top surfaces of the unknown sample 1 and the standard 2, respectively, as noted above. The thickness of sample 1 and the standard 2 must be known. This can be readily accomplished through exterior means by physical measurement, or for example done through additional instrumentation and sensors built into the testing apparatus (this is not shown in FIG. 1 since it is not necessary to the understanding of the concept).

Each heater means 3 and 4 should be of a type that provides, in this instance, controlled constant heat input to the sample 1 of unknown purity and to the gold standard 2, as opposed to a constant temperature source (the later case is subsequently discussed); the heat thus applied is a controlled amount and the heating elements 3 and 4, by their physical nature, each have low heat capacity so that all of the heat generated therein is transferred to the sample 1 and the standard 2.

If the temperature is measured at x=0, the surface opposite from the heated surface, equation (1) becomes:

$$T(t)=QL/k\{\alpha t/L^2 - 1/6 - 2/\pi^2 \Sigma_{m=1}^{\infty}(-1)^m/m^2[\exp(-\alpha m^2\pi^2 t/L^2)]\} \quad (1A)$$

If an attempt is made to counterfeit a sample, the weight W in pounds and the thickness L in feet, can be duplicated or can easily be measured. Thus, equation (1A) becomes:

$$T(t)=q/W\{t/c - L^2\rho/6k - 2L^2\rho/\pi^2 k\Sigma_{m=1}^{28}(-1)^m/m^2[\exp(-\alpha m^2\pi^2 t/L^2)]\} \quad (1B)$$

Where: q is the suddenly applied constant heat flux in BTU/sec and all other terms are as previously defined.

For proof of the purity of the sample it is sufficient that at all times during the test interval, the measured temperature of the suspected counterfeit bullion, or coupon, or coin sample be as high as that of the known gold standard (or a recording thereof). If the sample in question has the same purity as the standard, then it will be as hot as or hotter than the standard for comparison. This is subject to several restrictions and possible errors are taken up in the next paragraph.

Figure 3:
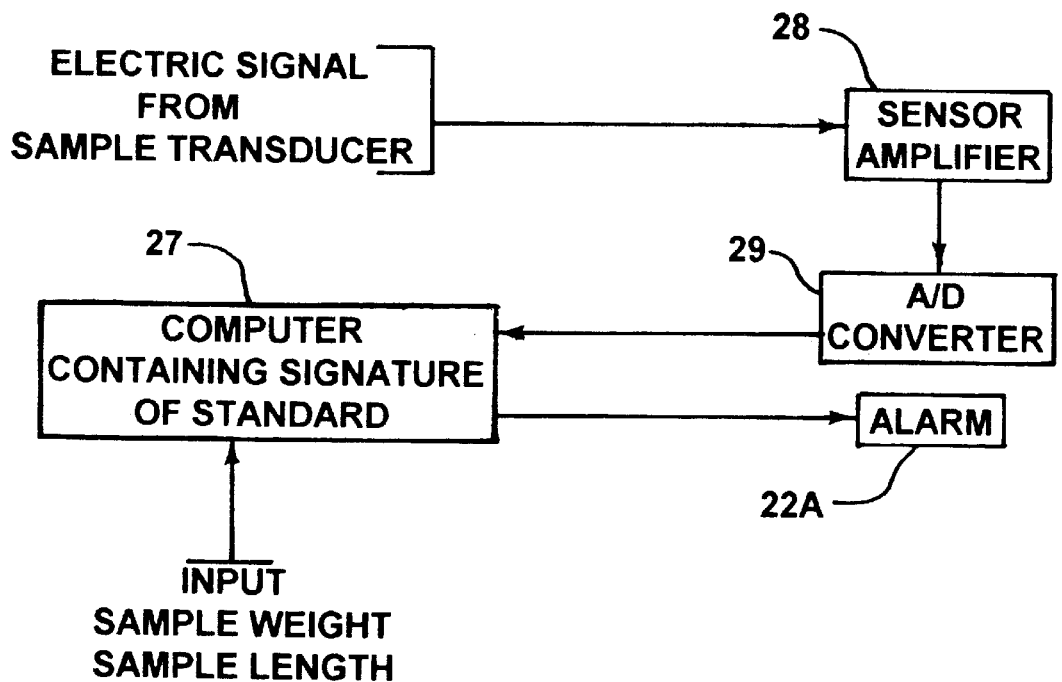
FIG. 3 shows in block diagram form another modified version of a part of the system of FIG. 1.

Use of equation (1B) requires that the ratio $q_{sa}/W_{sa}=q_{st}/W_{st}$ (wherein $q_{sa}$ and $q_{st}$ are the heat inputs to the sample and standard of respective weights $W_{sa}$ and $W_{st}$) must be kept within acceptable tolerance. The test is as good as the exactitude with which the thickness and weights are known. It may be impracticable to match thickness and weights of the test sample and the standard for comparison. However, neither is it necessary that the standard actually be present at the time the sample is tested nor is it necessary that a difference amplifier be employed since present day computers can readily discriminate between the temperature-time signatures and determine differences. Thus, in FIG. 3, one input to the computer 27 allows the measured thickness and weight of the sample and has stored within it the signatures of an equivalent standard, see Senturia et al, U.S. Pat. No. 3,747,755, which is incorporated by reference. Note the measurement of thickness and weight can be integral to the test device (for simplicity this is not shown in FIG. 1) and automatically programmed into the computer 27, as shown in FIG. 3, or be manually programmed. The second input, resulting in a time-varying temperature pattern of the sample, is converted to an electric signal as before and is fed to sensor amplifier 28 and thence to an analog-to-digital converter 29, the output of the converter being connected as the second input back to the computer 27. The two signatures, one from the standard and the other from the sample, are compared by the computer; filed and recorded for viewing, and connected to an alarm 22A.

Figure 4:
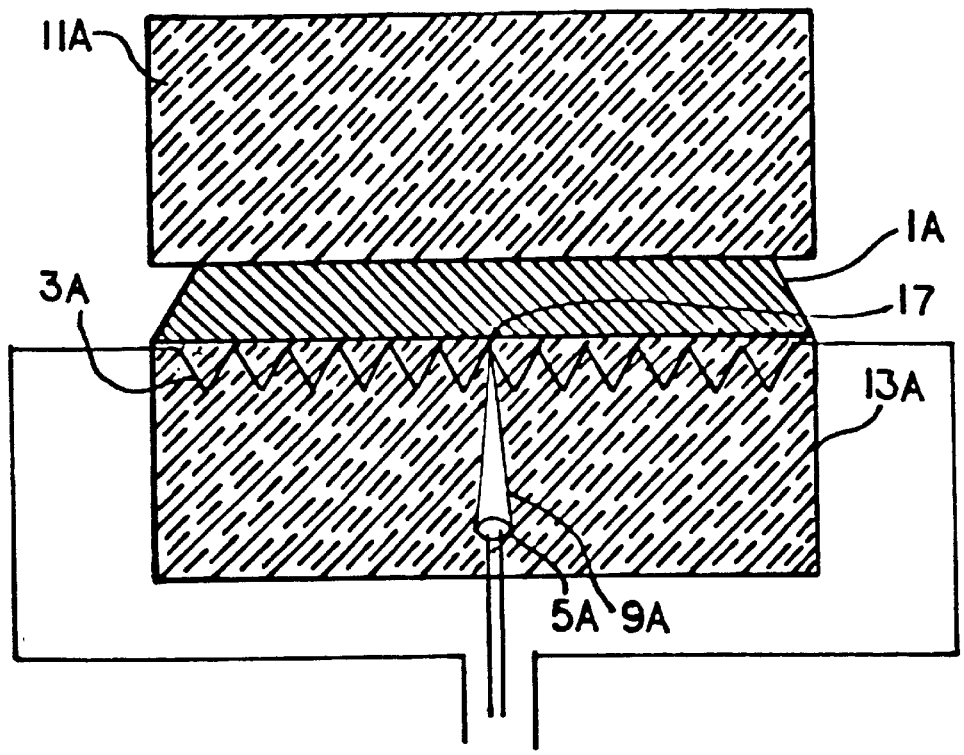
FIG. 4 shows a modification of the system shown in FIG. 1.

The embodiment indicated in the partly cut-away schematic, FIG. 4, shows as before the heating element 3A, within the insulation 13A, in full contact with the bottom surface of the test sample 1A and the top surface of the sample 1A is insulated by insulation 11A from the environment. If the temperature is measured at the middle of the heated surface at x=L of the sample, as indicated by the sensor 9A with focusing element 5A focused on a spot 17, then equation (1) becomes:

$$T(x,t) = QL/k\{\alpha t/L^2 + 1/3 - 2/\pi^2 \Sigma_{m=1}^{28} (-1)^m/m^2 [\exp(-\alpha m^2 \pi^2 t/L^2)] \cos(m\pi)\} \quad (1C)$$

The temperature sensor 9A is operatively disposed to sense the time-varying temperatures at the lower surface of sample 1A and thus provide as an output an electrical signal that is a function of the time-varying temperature. For this situation, only the thickness of test sample 1A is needed and its weight need not be known. As before, the thickness of the test sample 1A can be predetermined by physical measurement or a sensor built into the system with supplementary instrumentation. This is neither shown nor discussed here and is not further mentioned with reference to subsequently described systems, because it is not necessary to the understanding of the present concepts.

It is noted that the heating element 3A, shown in FIG. 4, can easily be replaced by either a focused laser or a focused infrared heater and equation 1C above will still be applicable. The definition of Q is defined by the knowledge of the area of the spot at which the heater is focused.

Note also, that the physical system associated with the standard is not shown in FIG. 4, nor need it be, because as already explained in the description of FIG. 1, an electronic signal representative of the standard's temperature-time signature, i.e., temperature-time curve, can readily be built into the electronics of the system; this was included in the discussions of FIGS. 2 and 3. Therefore, subsequent discussions of related embodiments and figures will include only the physical system associated with the sample to be tested.

As stated in U.S. Pat. No. 3,981,175 most adulterated samples will be cooler than the pure gold standard at the far end when x=0 (also at the heated end at x=L), but not always. In the course of the work leading to and arising from the aforementioned patent it was necessary to adjust the length of the sample and standard, which were in the form of rods, and the time of the test in order that an adulterated sample would always be cooler than the standard. In this work that choice is not available because the thickness, L, for bullion, coupons and discs (coins) are all different and fixed. For example, Handy and Harman Corporation produce gold bullion that range from a thickness of 3/16 inch (4.76 mm) to 1 ½ inches (38.10 mm) and gold coupons that range from a thickness of 0.039 inch (0.99 mm) to 1/16 inch (1.59 mm). Consequently, not all adulterated gold samples, when applying either Equation (1A), (1B) or (1C) were cooler than the gold standard after applying a pulse of heat for a given time interval.

The reason for this is that there appears to be an optimum combination of thermal properties as they occur in equation (1), and related equations (1A), (1B) and (1C), as a function of thickness and length of test time. These properties, important in controlling the transmission of heat through the body and thus the temperature, are thermal conductivity, k, and thermal diffusivity, $\alpha$; where $\alpha$ is defined as $k/\rho c$, $\rho$ being the density and c the specific heat. The thermal properties of gold and those elements most likely to be used as adulterants are presented in Table 1 below:

TABLE I

| Elements | $\rho$ lb/ft$^3$ | c BTU/lb-F | k BTU/hr-ft-F | $\alpha$ ft$^2$/hr |
|---|---|---|---|---|
| Gold (Au) | 1204.860 | 0.031 | 183.159 | 4.936 |
| Copper (Cu) | 559.355 | 0.092 | 231.693 | 4.483 |
| Silver (Ag) | 655.494 | 0.056 | 247.872 | 6.729 |
| Lead (Pb) | 705.436 | 0.031 | 20.396 | 0.948 |
| Tungsten (W) | 1204.860 | 0.032 | 100.535 | 2.591 |

Ratios of from 50% gold (Au) and 50% adulterants, each of: copper (Cu), silver (Ag), lead (Pb) or tungsten (W), to ratios of 99.5% Au and 0.5% adulterants, each of Cu, Ag, Pb or W in bullion thickness from 3/16 inch (4.76 mm) to 1 ½ inches (38.10 mm) and coupons and coin of from a thickness of 0.039 inch (0.95 mm) to 1/16 inch (1.67 mm) were examined. A linear relationship was used to estimate the thermal properties of the various ratios of adulterants examined. White and yellow gold samples of 14, 15, 18 and 22 carats were also tested and compared to pure gold (24 carat).

The samples that defeated the test set forth in equation (1), because of their particular combination of thermal properties and the length of the test times, as well as required thickness, were composed of the adulterant Pb. However, when these same samples were tested in accordance with equation (2), where a constant temperature $T_0$ was applied for a given time period, they were cooler than the gold standard. The basic reason for this is that pure gold has a higher thermal diffusivity, a, than any of the aforementioned admixtures of gold samples with the exception of a silver admixture. Yet, the silver admixture did not pass the first test, i.e., application of equation (1). Therefore, with the use of the two tests, which is considered the uniqueness of the invention, referred here as the dual test method, i.e., the application of both general equations (1) and (2), will discriminate between the pure standard and the adulterated sample of at least 99.5 percent purity.

With further reference to equation (2); pure silver has the highest thermal diffusivity of any known metallic material, and thus as a function of time, fine silver bullion of up to 3 ¼ inch (82.55 mm) thick, including coin of up to 99.5 percent purity will attain a higher far end temperature than any other admixture. The U. S. Standard of 90 percent silver, the Sterling Standard of 92.5 percent purity and the Britannia Standard of 95.83 percent purity, can also be used as successful paradigms for comparison. Therefore, it is sufficient that at any time during the test, the temperature of the known silver bullion, coupon or coin (or a recording thereof) be as low as or lower than that of the test sample, for certainty that the sample in question is either as pure or purer than the standard. This is subject to restrictions and several possible errors, as now discussed.

The constant temperature $T_0$ in equation (2), which can be applied by the use of a heat sink or an unlimited source of heat at a surface for a defined time, must be identical for the sample and the standard. The test is as good as the exactitude with which the thickness of the bullion, coupons and discs (coins) are known. The thermal diffusivity of silver is very high compared to most materials, as shown in Table I. (Those elements shown in Table I as possible adulterants of gold are also candidates likely to be used as forgeries of silver.) As in the case of the gold test, the thickness of the sample L in equation (2), is very important for the sensitivity of the test. Nevertheless, more sensitive instrumentation and amplification of temperature differences can compensate for thin samples.

Further embodiments can be realized by determining the slopes of the temperature-time curves; these objectives can readily obtained by taking the first derivative of the various appropriate equations. This is accomplished in the following:

Differentiating equation (1), the general equation applicable to FIGS. 1 and 4, we obtain:

$$dT/dt = Q/\rho cL\{1 + 2\Sigma_{m=1}^{\infty}(-1)^m \exp(-\alpha m^2\pi^2 t/L^2 t)\cos(m\pi x/L)\} \quad (3)$$

However, at both x=0 and x=L equation (3) reduces to:

$$dT/dt = Q/\rho cL \quad (3A)$$

Similarly, equation (1B) reduces to:

$$dT/dt = \rho/Wc \quad (3B)$$

To determine the slope of a system where constant temperature is applied and where the system is completely enclosed in an insulated medium or as shown in FIG. 1, differentiation of equation (2), with x=0, will result in the following:

$$dT/dt = T_0 L/(\pi\alpha t^3)^{1/2} \Sigma_{n=0}^{\infty}(-1)^n(2n+1)\exp[-(2n+1)^2/4\alpha t/L^2] \quad (4)$$

If in the system shown in FIGS. 1 and 4 the heat is turned off, referred here as the decay rate, the temperature of the slab becomes:

$$T = Qt/\rho cL \quad (5)$$

Differentiating equation (5) gives the slope of the decay rate as:

$$dT/dt = Q/\rho cL \quad (5A)$$

Equations (3), (3A), (3B), (5) and (5A) provide a further check on the authenticity of the previously described gold and silver bullion, coupons, and discs. Using the dual test method indicated by equations (3A) and (4), the slopes for the constant heat and constant temperature applications, respectively, will provide a further check on the authenticity of the sample. Although the formulations for the decay rate and its slope for the constant temperature application are not presented here, nevertheless, such tests appropriately combined with those indicated by equations (5) and (5A), will provide a further check on the authenticity of the previously described gold and silver bullion, coupons, and discs.

Appropriate instrumentation can be employed with the use of the above mentioned tests and equations providing guidelines. For example, additional instrumentation, such as a differentiator (not shown), can be added between the sensor amplifier 28 and the A/D convertor 29 to the circuitry in FIG. 3 to differentiate the temperature-time signal from the sample transducer to obtain slope versus time signals analogous to equations (3A), (3B) and (4). These signatures can then be compared to the appropriately stored data in the computer 27; filed and recorded for viewing, and connected to the alarm 22A. Alternatively, rather than include a differentiator in the circuitry, the computer can numerically differentiate the digitized temperature-time signal from the A/D converter 29 and thus the process will proceed as aforementioned.

The decay rate versus time signatures can also be obtained by simply retaining the electric signal from the sample transducer 9 after the heating element 3 in FIG. 1 has been shut off. The process for the attainment of the decay rate versus time signatures will proceed as aforementioned and the slope of decay rate would then proceed as previously described in the above paragraph.

Figure 5:
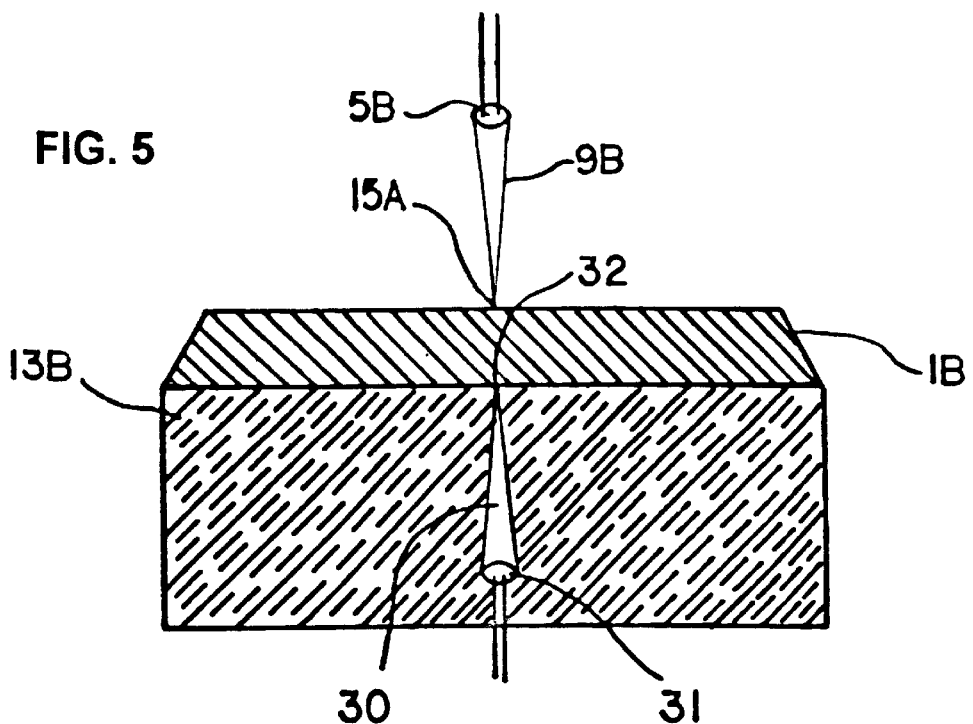
FIG. 5 shows a modification of the system shown in FIG. 4.
Figure 6:
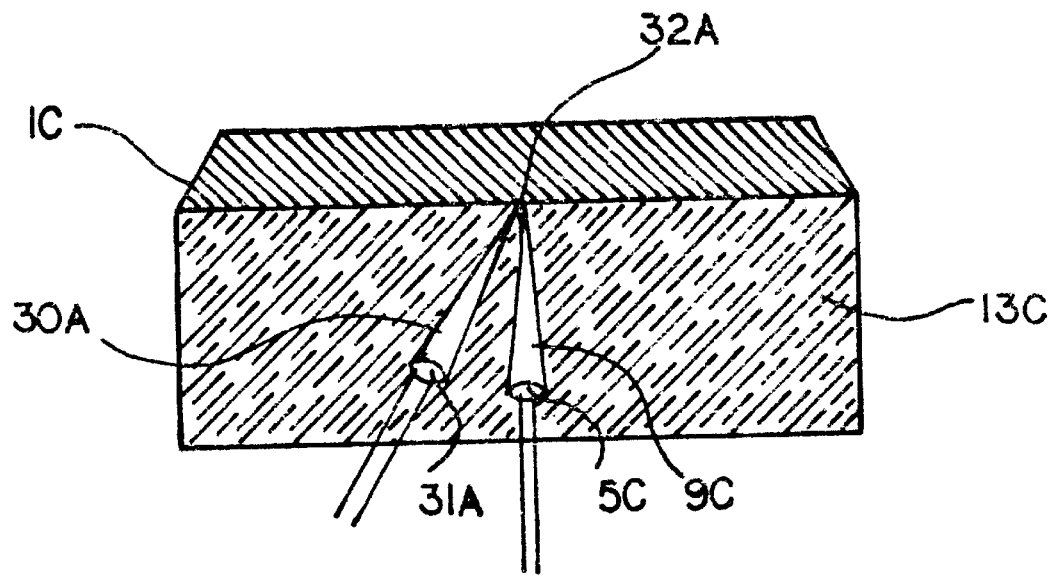
FIG. 6 shows a modification of the system shown in FIG. 5.

If the areal dimensions of the test item are relatively large compared to its thickness, then another embodiment and improvement, schematically shown in FIGS. 5 and 6, is realized, i.e., exposure of the sample at x=0 to the environment.

The general heat transfer equation for the body shown in FIGS. 5 and 6, i.e., constant heat flux Q applied at x=L and whose opposite surface is exposed to a medium, is:

$$T(x,t) = Q/k\{1/h + x - 2\Sigma_{n=1}^{\infty}\exp(-\alpha\beta^2{}_n t)\cos[(L-x)\beta_n](\beta^2{}_n + h^2)/(\beta^2{}_n[h + L(\beta^2{}_n + h^2)])\} \quad (6)$$

Where the thermal constants are as previously defined and h=H/k; H is the coefficient of heat transfer as a function of temperature in BTU/sec-ft²–F and $\beta_n$, n=1,2,3 . . . nth, are the positive roots of the transcendental equation $\beta\tan\beta L = h$. (See Carslaw and Jaeger *Conduction of Heat in Solids*, Oxford Press, 1950).

Returning to FIG. 5, the sample 1B being testing has its upper surface free of insulation. The sample 1B is placed on an insulated bed 13B enclosing a non-contacting heat source such as a laser or infrared heat source 30 and a focusing means 31, which is concentrated on a known small area 32 at the mid-lower surface of a bullion, coupon or a coin 1B. The sensing function is provided by infrared temperature sensor 9B focused by a focusing means 5B on a spot 15A directly in line with spot 32. The temperature sensor 9B is operatively disposed to sense the time-varying temperatures at the upper surface of sample 1B and thus provide as an output an electrical signal that is a function of the time-varying temperature. For this situation, only the thickness of the test sample is needed and its weight need not be known.

When the temperature is measured at x=0, as indicated in FIG. 5, equation (6) becomes:

$$T(x,t) = Q/k\{1/h - 2\Sigma_{n=1}^{28}\exp(-\alpha\beta^2{}_n t)\cos(L\beta_n)(\beta^2{}_n + h^2)/(\beta^2{}_n[h + L(\beta^2{}_n + h^2)])\} \quad (6A)$$

A variation of FIG. 5 shows a partly cut-away schematic, FIG. 6, where again the sample 1C is placed on an insulated bed 13C with the noncontacting laser or infrared heater 30A being focused by focusing means 31A which is concentrated on a small known area 32A at the mid-lower surface of a bullion, coupon or a coin. The sample being tested has its upper surface free of insulation and the temperature is sensed by an infrared temperature sensor 9C focused by a focusing means 5C at the lower surface on the spot 32A.

When the temperature is measured at x=L, the same surface at which the heat is applied, as depicted in FIG. 6, equation (6) becomes:

$$T(x,t) = Q/k\{1/h + L - 2\Sigma_{n=1}^{\infty}\exp(-\alpha\beta^2{}_n t)(\beta^2{}_n + h^2)/(\beta^2{}_n[h + L(\beta^2{}_n + h^2)])\} \quad (6B)$$

A similar situation as that described above for FIG. 5, where instead of a sudden pulse of heat, a constant temperature source T(t) is applied to silver bullion or disc (coin); the formula for this case, given by the same authors (Carslaw and Jaeger), is:

$$T=T_0\{1/(1+hL)-2\Sigma_{n=1}^{\infty}\exp(-\alpha\gamma^2_n t)\sin(L\gamma_n)(\gamma_n^2+h^2)/(\gamma_n[h+L(\gamma^2_n+h^2)])\} \quad (7)$$

Where $\gamma_n$, n=1,2,3 ... nth, are the positive roots of the transcendental equation $\gamma\cot\gamma L+h=0$.

Equations (6A) and (6B) were employed to determine the temperature differences between the idealized gold standard and adulterated gold samples at the surfaces opposite the application of constant heat at x=0 and at the heated surfaces at x=L, respectively. The value of H used was 1.30 to 1.70 BTU/hr-ft$^2$-F, obtained from *Heat Transmission*, McGraw-Hill, 2nd ed., 1942, for polished surfaces in still air with small temperature differences. The thermal properties of the elements used were those given in Table I, as well as the same percent variation previously utilized when applying equation (1). Results of testing the samples according to equations (6A) and (6B), again indicated only the sample containing Pb defeated the test comprised of the previously mentioned thickness of bullion, coupon and coin at both x=0 and x=L. Nevertheless, when these samples containing variations of Pb were tested in accordance to equation (7), where constant temperature was applied for a given time period at x=L and the temperature measured at x=0, they were lower in temperature than the idealized pure gold standard tested under the same circumstances. The first test (constant energy) will generally discriminate between the idealized gold standard and most adulterated samples with exception of those compositions comprised of gold and lead. However, when a retest (constant temperature) is applied it will show that such compositions are fraudulent.

Additional embodiments can be realized by determining the slopes of the temperature-time curves, again these objectives can readily be obtained by taking the first derivative of the various appropriate equations. This is accomplished in the following:

Again by differentiating equation (6A), which is applicable to FIG. 5 when x=0:

$$dT/dt=2Q/\rho c\Sigma_{n=1}^{\infty}\exp(-\alpha\beta^2_n t)\cos(L\beta_n)(\beta^2_n+h^2)/[h+L(\beta^2_n+h^2)], \quad (8)$$

and differentiating equation (6B), where x=L, which is appropriate for FIG. 6:

$$dT/dt=2Q/\rho c\Sigma_{n=1}^{\infty}\exp(-\alpha\beta^2_n t)(\beta^2_n+h^2)/[h+L(\beta^2_n+h^2)] \quad (9)$$

The slope at x=0 opposite to the surface which is exposed to the environment and at which a constant application of temperature is applied, analogous to FIG. 5, is obtained by differentiating equation (7):

$$dT/dt=2T_0\alpha\Sigma_{n=1}^{\infty}\gamma_n\exp(-\alpha\gamma^2_n t)\sin(L\gamma_n)(\gamma_n^2+h^2)/[h+L(\gamma^2_n+h^2)] \quad (10)$$

Equations (8), (9) and (10) with the use of the dual test method, also provide a further check on the authenticity where appropriately applied to the previously described gold and silver bullion, coupons, and discs.

The formulations are not presented for the decay rates and their slopes after the removal of the sudden heat pulse application and after the removal of constant temperature application, appropriate to FIGS. 5 and 6. Nevertheless, such tests along with the use of the dual test method and the suitable instrumentation, previously described, can be employed to provide a further check on the authenticity of the gold and silver bullion, coupons, and discs.

Heretofore, there has been no simple, viable method of nondestructively determining the purity of gold or silver jewelry, such as rings or other shapes. Jewelry items, whose shapes are analogous to bullion already depicted, for example FIGS. 4 or 5, i.e., signets of gold or silver rings, or other shapes that conform to the ratios previously mentioned of unknown fineness for which it is desired to know their carat or silver purity can also be examined by the method already described. If the gold or silver rings have signet portions or even other shapes in which their dimensions, such as widths and lengths or diameters that are a ratio of approximately 3/1 or greater compared to their thickness, then these test items can be considered as slabs when pulsed by a suddenly applied constant heat source or the application of a constant temperature and compared to a standard tested under the same circumstances.

The calibration of the standard can be attained by simply fabricating the jewel item from the desired fineness for comparison. A gold standard, being considered either 24, 22, 18, 14 or even 9 carat gold, or a Sterling or Britannia Standard from which the temperature-time signature of the exact replica of the test sample having already been attained. As indicated previously the temperature-time signature of the standard can readily be built into the system instrumentation and need not be discussed further.

Figure 7:
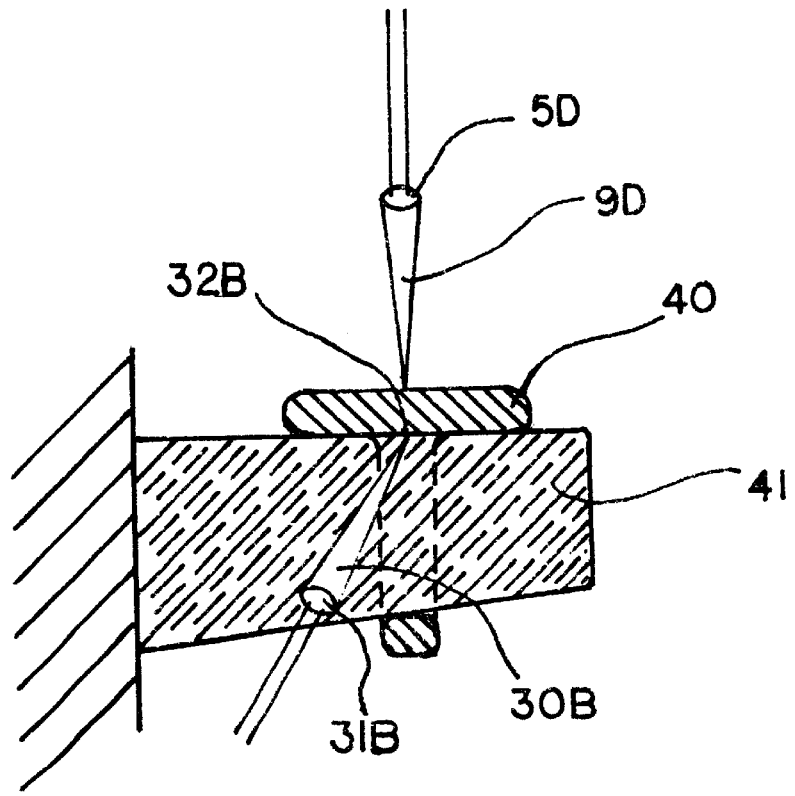
FIG. 7 schematically shows a partly cut-away system to determine the purity of a material sample in the form of a ring.

Analogous to the systems shown in FIGS. 1 and 5, is the aforementioned gold or silver ring sample 40, shown in FIG. 7, which can be slipped over an insulated semi-tapered mandrel 41. The sample being tested has its upper surface and edges free of insulation. The heating function can be supplied by a laser or an infrared heater (30B) focused by a focusing means (31B) on to a small known area 32B at the mid-lower surface of the signet and the sensing function is provided by an infrared temperature sensor 9D and a focusing means 5D. The temperature sensor is operatively disposed to sense the time-varying temperatures at the small known area 32B of the signet and thus provides as output an electrical signal that is a function of the time-varying temperature. For this situation, only the thickness of the signet portion of the test sample is needed, but its weight need not be known.

Additional variations of FIG. 7 can be envisioned: With the heating function within the insulated semi-tapered mandrel and focused on the mid-inside surface of the signet and measure the temperature at the same location, similar to FIG. 6, or the heating function focused on the mid-outside surface of the signet and the temperature measured at the same location or on the inside mid-surface of the signet.

It was found that the dual test according to equations (6A) and (6B), as well as equation (7), as described above, were successfully applied to a gold ring, such as that shown in FIG. 7, having 14, 18 and 24 carat alloys, which were used as standards to discriminate between such alloys and determine their carat content. Also in all cases, the adulterants of silver tested according to equation (7) showed lower temperature-time responses than those of pure silver and the silver standards.

Equations (8), (9) and (10), with the use of the dual test method, also provide a further check on the authenticity where appropriately applied to the above described gold and silver jewelry.

Again as previously mentioned, the formulations are not presented for the decay rates and their slopes after the removal of the sudden heat pulse application and after the removal of constant temperature application, appropriate to FIG. 7. Nevertheless, such tests along with the use of the dual test method and the suitable instrumentation, previously described, can be employed to provide a further check on the authenticity of the above described gold and silver jewelry.

Figure 8:
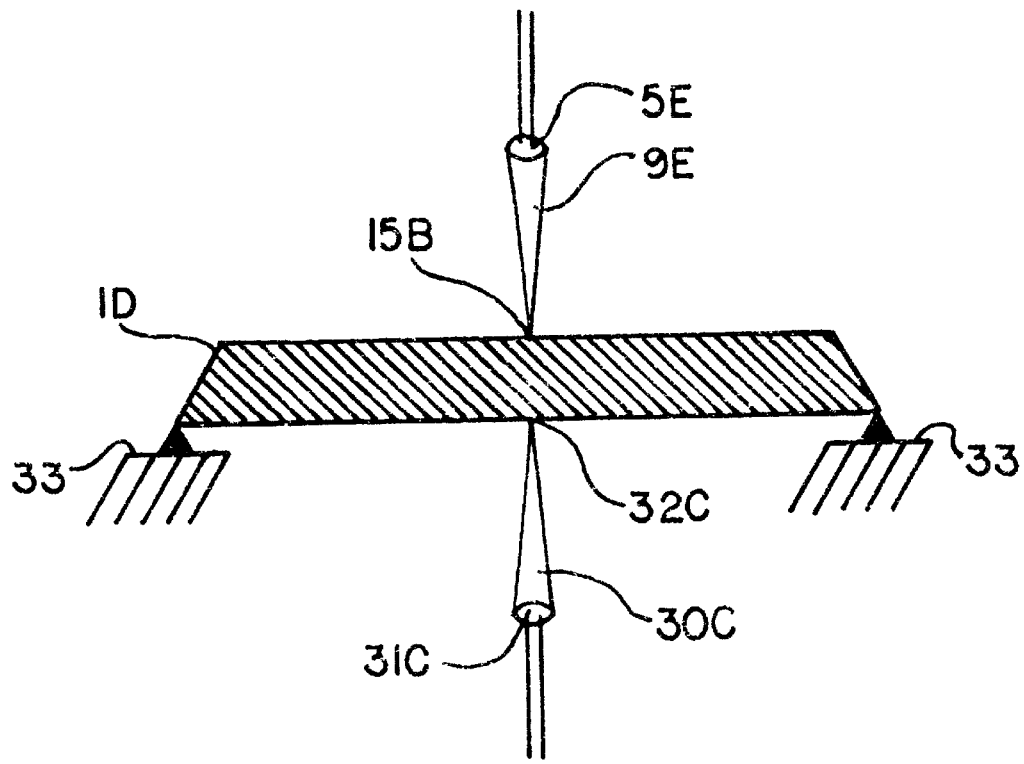
FIG. 8 shows a modification of the system shown in FIG. 5.
Figure 9:
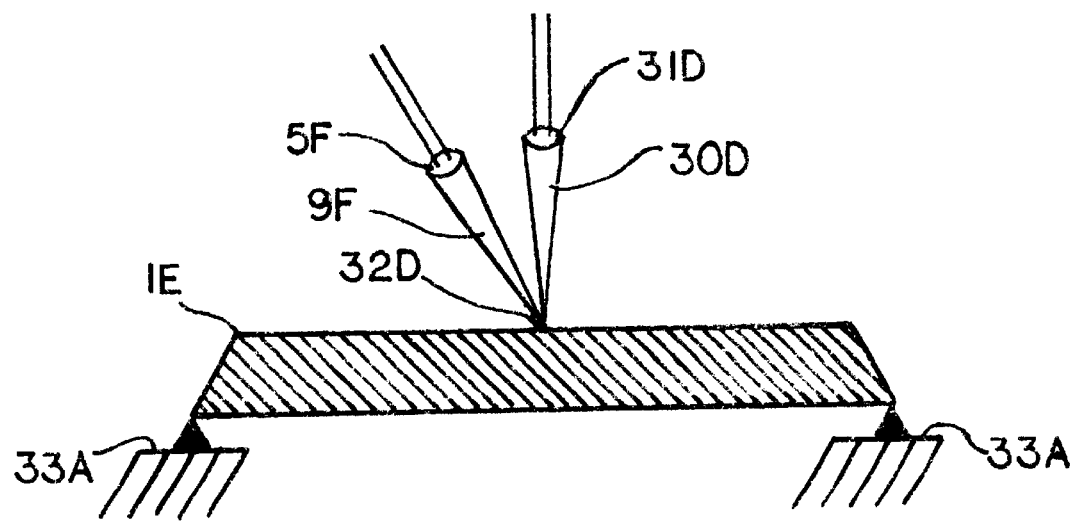
FIG. 9 shows a modification of FIG. 6.

Test samples that are not insulated, as schematically depicted in FIGS. 8 and 9, can also be tested even though the formulation is not presented here. Nevertheless, the results will be similar to those cases already described but the magnitudes of the resulting temperatures will be mitigated. However, with present day instrumentation the signals can be readily amplified such that the difference between the standard and the test sample will be measurable.

Turning to FIG. 8, the test sample 1D is place on supports 33 with the non-contacting laser or infrared heater 30C being focused by focusing means 31C which are concentrated on a small known area 32C at the mid-lower surface of a bullion, coupon or a coin 1D. The sample 1D has at its upper surface an infrared temperature sensor 9E and focusing means 5E focused on a spot 15B opposite 32C, and as before the temperature sensor 9E and its focusing means 5E detect the temperature-time response of the sample which is compared to the temperature-time signature of the standard having been tested under the exact conditions as the test sample 1D for comparison.

Now turning to FIG. 9, the test sample 1E is place on supports 33A with the non-contacting laser or infrared heater 30D being focused by focusing means 31D which are concentrated on a small known area 32D at the mid-upper surface of a bullion, coupon or a coin 1E. The sample 1E being testing also has at its upper surface an infrared temperature sensor 9F and focusing means 5F and the temperature sensor is focused on the small area 32D and it detects the temperature-time response of the test sample 1E which is compared to the temperature-time response signature of the standard having been tested under the exact conditions as the test sample for comparison.

Again, other embodiments can be described as jewelry samples, whose shapes are analogous to the bullion depicted in FIGS. 8 and 9, i.e., the signets of gold rings or silver rings of unknown fineness for which it is desired to know their carat or silver purity. The. aforementioned gold or silver ring samples are suspended in air by gripping them at locations opposite from the signets. The sample being tested has at its lower surface, analogous to FIG. 8, an infrared heater or laser focused on a spot of known area in the middle of the signet and the sensing function is provided by an infrared temperature sensor focused on the top surface of the signet opposite to the focused heater. The alternative system, which is analogous to FIG. 9, would have the sample being tested at its upper surface with an infrared heater or laser focused on a spot of known area at the middle of the signet and the sensing function, provided by an infrared temperature sensor and is focused on a the same spot on the upper surface. The temperature sensors are operatively disposed to sense the time-varying temperatures at their respective surfaces of the signets and thus provide as output electrical signals that are a function of the time-varying temperature which is compared to the temperature-time signature of the standard having been tested under the exact conditions as the test sample for comparison.

For the situations described above, i.,e., FIGS. 8 and 9, and the similar systems such as the jewelry test sample, only the thickness of the bullion and signet portion of the rings are needed, but their weights need not be known. It is further noted that even though the formulation, i.e., temperature-time signatures, slopes versus time signatures, decay rate and slopes of the decay rate versus time signatures for both sudden heat pulse application and for constant temperature application are not presented, nevertheless, such tests along with the use of the dual test method and the suitable instrumentation previously described can be employed to provide a further check on the authenticity of the previously described gold and silver bullion, coupons, discs and jewelry.

What is claimed is:

1. A method for determining nondestructively the purity of a test object of unknown purity, the method comprising the steps of:

providing said test object, said test object having a given geometric configuration;

applying a constant quantity of energy to a first given location on said test object during a first defined time having a first time duration, thereby causing a temperature change resulting in a constant-energy-input temperature-time signature at a first given measuring spot on said test object;

measuring said constant-energy-input temperature-time signature at said first given measuring spot;

applying a constant temperature input to a second given location on said test object during a second defined time having a second time duration, thereby causing a temperature change resulting in a constant-temperature-input temperature-time signature at a second given measuring spot on said test object;

measuring said constant-temperature-input temperature-time signature at said second given measuring spot;

providing a standard object of known purity, wherein said standard object has a geometric configuration substantially corresponding to said given geometric configuration of said test object;

applying the same constant quantity of energy as applied to said test object to said standard object at a first corresponding location on said standard object during a defined time having said first time duration, thereby causing a temperature change resulting in a constant-energy-input temperature-time signature at a first corresponding measuring spot on said standard object;

measuring said constant-energy-input temperature-time signature at said first corresponding measuring spot;

applying the same constant temperature input as applied to said test object to said standard object at a second corresponding location on said standard object during a defined time having said second time duration, thereby causing a temperature change resulting in a constant-temperature-input temperature-time signature at a second corresponding measuring spot on said standard object;

measuring said constant-temperature-input temperature-time signature at said second corresponding measuring spot;

comparing said measured constant-energy-input temperature-time signature of said test object to said measured constant-energy-input temperature-time signature of said standard object resulting in a constant-energy-input test result;

comparing said measured constant-temperature-input temperature-time signature of said test object to said measured constant-temperature-input temperature-time signature of said standard object resulting in a constant-temperature-input test result; and determining the purity of said test object relative to said standard object based on both said constant-energy-input test result, measured at said first given measuring spot and said first corresponding measuring spot, and said constant-temperature-input test result, measured at said second given measuring spot and said second corresponding measuring spot.

2. The method of claim 1, wherein
each of the steps of measuring the temperature-time signatures of said test object comprise focusing a first non-contact temperature sensor configured to sense temperatures at said given measuring spots; and
each of the steps of measuring the temperature-time signatures of said standard object comprise focusing a second non-contact temperature sensor configured to sense temperatures at said corresponding measuring spots on said standard object.

3. The method of claim 2 further comprising:
recording each of said measured temperature-time signatures in a computer, thereby providing a computer recorded temperature-time signature of said test object during a temperature decay time and a computer recorded temperature-time signature of said standard object during a corresponding temperature decay time;
calculating a slope of said temperature-time signature of said test object during said temperature decay time by said computer;
calculating a slope of said temperature-time signature of said standard object during said corresponding temperature decay time by said computer; and
wherein the comparing steps further comprise comparing said slope of the temperature-time signature of said test object during the temperature decay time to said slope of the temperature-time signature of said standard object during the corresponding temperature decay time resulting in each of the respective of said constant-energy-input test result and said constant-temperature-input test result whereby the purity of said test object is determined.

4. The method of claim 2 further comprising:
recording each of said measured temperature-time signatures in a computer, thereby providing a computer recorded temperature-time signature of said test object and a computer recorded temperature-time signature of said standard object;
calculating a slope of said temperature-time signature of said test object by said computer;
calculating a slope of said temperature-time signature of said standard object by said computer; and
wherein the comparing steps further comprise comparing said slope of the temperature-time signature of said test object to said slope of the temperature-time signature of said standard object resulting in each of the respective of said constant-energy-input test result and said constant-temperature-input test result whereby the purity of said test object is determined.

5. The method of claim 1, wherein:
said constant quantity of energy is applied to said first given location on said test object by placing a heated object above ambient temperature in contact with said test object; and
said same constant quantity of energy is applied to said first corresponding location on said standard object by placing said heated object above ambient temperature in contact with said standard object.

6. The method of claim 1, wherein;
said constant quantity of energy is applied to said first given location on said test object with a non-contact focused input of constant energy of constant heat flux; and
said same constant quantity of energy is applied to said first corresponding location on said standard object with a non-contact focused input of constant energy of constant heat flux.

7. The method of claim 1, wherein:
said constant quantity of energy is applied to said first given location on said test object with a first focused laser; and
said same constant quantity of energy is applied to said first corresponding location on said standard object with a second focused laser.

8. The method of claim 1, Wherein:
said constant quantity of energy is applied to said first given location on said test object by a heating coil configured to be placed in contact with the surface of said test object at said first given location; and
said same constant quantity of energy is applied to said first corresponding location on said standard object by a heating coil configured to be placed in contact with the surface of said standard object at said first corresponding location.

9. The method of claim 1, wherein:
said constant temperature input is applied to said second given location on said test object by placing a heat sink in contact with said test object; and
said same constant temperature input is applied to said second corresponding location on said standard object by placing said heat sink in contact with said standard object.

10. The method of claim 1, wherein said constant-energy-input test result is determined based on two sets of measurements, including:
a first set, wherein
said first given measuring spot is at the same location on said test object as said first given location at which said constant quantity of energy is applied; and
said first corresponding measuring spot is at the same location on said standard object as said first corresponding location at which said same constant quantity of energy is applied; and
a second set wherein
said first given measuring spot is at a different location on said test object as said first given location at which said constant quantity of energy is applied; and
said first corresponding measuring spot is at a different location on said standard object as said first corresponding location at which said same constant quantity of energy is applied.

11. The method of claim 1, wherein:
said constant quantity of energy is applied to said first given location on said test object by applying an object, liquid, or liquefied gas chilled below ambient temperature in contact with said test object, thereby causing a temperature decrease resulting in said constant-energy-input temperature-time signature at said first given measuring spot on said test object; and
said same constant quantity of energy is applied to said first corresponding location on said standard object by applying said object, liquid, or liquefied gas chilled below ambient temperature in contact with said standard object thereby causing a temperature decrease resulting in said constant-energy-input temperature-time signature at said first corresponding measuring spot on said standard object.

12. The method of claim 1 further comprising:

recording each of said measured temperature-time signatures in a computer, thereby providing a computer recorded temperature-time signature of said test object during a temperature decay time and a computer recorded temperature-time signature of said standard object during a corresponding temperature decay time;

calculating a slope of said temperature-time signature of said test object during said temperature decay time by said computer;

calculating a slope of said temperature-time signature of said standard object during said corresponding temperature decay time by said computer; and wherein the comparing steps further comprise comparing said slope of the temperature-time signature of said test object during the temperature decay time to said slope of the temperature-time signature of said standard object during the temperature decay time resulting in each of the respective of said constant-energy-input test result and said constant-temperature-input test result whereby the purity of said test object is determined.

13. The method of claim 1 further comprising:

recording each of said measured temperature-time signatures in a computer, thereby providing a computer recorded temperature-time signature of said test object and a computer recorded temperature-time signature of said standard object;

calculating a slope of said temperature-time signature of said test object by said computer;

calculating a slope of said temperature-time signature of said standard object by said computer; and wherein the comparing steps further comprise comparing said slope of the temperature-time signature of said test object to said slope of the temperature-time signature of said standard object resulting in each of the respective of said constant-energy-input test result and said constant-temperature-input test result whereby the purity of said test object is determined.

14. The method of claim 1, wherein said constant-temperature-input test result is determined based on two sets of measurements, including:

a first set, wherein
said second given measuring spot is at the same location on said test object as said second given location at which said constant temperature input is applied; and
said second corresponding measuring spot is at the same location on said standard object as said second corresponding location at which said same constant temperature input is applied; and a second set wherein
said second given measuring spot is at a different location on said test object as said second given location at which said constant temperature input is applied; and
said second corresponding measuring spot is at a different location on said standard object as said second corresponding location at which said same constant temperature input is applied.

15. An apparatus for determining nondestructively the purity of a test object of unknown purity, said test object having a given geometric configuration, the apparatus comprising:

means for applying a constant quantity of energy to a first given location on said test object during a first defined time having a first time duration, thereby causing a temperature change resulting in a constant-energy-input temperature-time signature at a first given measuring spot on said test object;

means for measuring said constant-energy-input temperature-time signature at said first given measuring spot;

means for applying a constant temperature input to a second given location on said test object during a second defined time having a second time duration, thereby causing a temperature change resulting in a constant-temperature-input temperature-time signature at a second given measuring spot;

means for measuring said constant-temperature-input temperature-time signature at said second given measuring spot;

a standard object of known purity, wherein said standard object has a geometric configuration substantially corresponding to said given geometric configuration of said test object;

means for applying the same constant quantity of energy as applied to said test object to said standard object at a first corresponding location on said standard object during a defined time having said first time duration, thereby causing a temperature change resulting in a constant-energy-input temperature-time signature at a first corresponding measuring spot on said standard object;

means for measuring said constant-energy-input temperature-time signature at said first corresponding measuring spot;

means for applying the same constant temperature input as applied to said test object to said standard object at a second corresponding location on said standard object during a defined time having said second time duration, thereby causing a temperature change resulting in a constant-temperature-input temperature-time signature at a second corresponding measuring spot on said standard object;

means for measuring said constant-temperature-input temperature-time signature at said second corresponding measuring spot;

means for comparing said measured constant-energy-input temperature-time signature of said test object to said measured constant-energy-input temperature-time signature of said standard object resulting in a constant-energy-input test result;

means for comparing said measured constant-temperature-input temperature-time signature of said test object to said measured constant-temperature-input temperature-time signature of said standard object resulting in a constant-temperature-input test result; and means for determining the purity of said test object relative to said standard object based on both said constant-energy-input test result, measured at said first given measuring spot and said first corresponding measuring spot, and said constant-temperature-input test result, measured at said second given measuring spot and said second corresponding measuring spot.

16. The apparatus of claim 15, wherein each of said means for measuring said temperature-time signatures of said test object comprise a first focused non-contact temperature sensor configured to sense temperatures at said given measuring spots; and each of said means for measuring said temperature-time signatures of said standard object comprise a second focused non-contact temperature sensor configured to sense temperatures at said corresponding measuring spots on said standard object.

17. The apparatus of claim 15, wherein:

said means for applying a constant quantity of energy to said first given location on said test object comprises a first laser focused at said first given location; and said means for applying the same constant quantity of energy as applied to said test object to said standard object comprises a second laser focused at said first corresponding location on said standard object.

18. The apparatus of claim 15, wherein said means for applying a constant quantity of energy to said first given location on said test object comprises a heating coil configured to be placed in contact with the surface of said test object at said first given location; and said means for applying the same constant quantity of energy as applied to said test object to said standard object comprises a heating coil configured to be placed in contact with the surface of said standard object at said first corresponding location.

19. The apparatus of claim 15, wherein said constant-quantity of energy-input test result is determined based on two sets of measurements, including:

a first set, wherein said first given measuring spot is at the same location on said test object as said first given location at which said constant quantity of energy is applied; and said first corresponding measuring spot is at the same location on said standard object as said first corresponding location at which said same constant quantity of energy is applied; and a second set wherein said first given measuring spot is at a different location on said test object as said first given location at which said constant quantity of energy is applied; and said first corresponding measuring spot is at a different location on said standard object as said first corresponding location at which said same constant quantity of energy is applied.

20. The apparatus of claim 15, wherein said constant-temperature-input test result is determined based on two sets of measurements, including:

a first set, wherein said second given measuring spot is at the same location on said test object as said second given location at which said constant temperature input is applied; and said second corresponding measuring spot is at the same location on said standard object as said second corresponding location at which said same constant temperature input is applied; and a second set wherein said second given measuring spot is at a different location on said test object as said second given location at which said constant temperature input is applied; and said second corresponding measuring spot is at a different location on said standard object as said second corresponding location at which said same constant temperature input is applied.

* * * * *

UNITED STATES PATENT AND TRADEMARK OFFICE
CERTIFICATE OF CORRECTION

PATENT NO. : 6,431,748 B1
DATED : August 13, 2002
INVENTOR(S) : Francis I. Baratta It is certified that error appears in the above-identified patent and that said Letters Patent is hereby corrected as shown below:

Column 12,
Line 8, "AID" should be -- A/D. --

Column 15,
Line 40, the period after the word "the" should be deleted.

The following columns and line numbers that correspond to the numbered equations are shown corrected in the attached pages and are to replace such numbered equations in the patent:
Column 4, lines 22-23, Eq. (1)
Column 4, line 45, Eq. (2)
Column 8, line 37, Eq. (1A)
Column 8, lines 42-43, Eq. (1B)
Column 9, lines 27-28, Eq. (1C)
Column 11, line 23, Eq. (3)
Column 11, line 37, Eq. (4)
Column 12, lines 26-27, Eq. (6)
Column 12, lines 52-53, Eq. (6A)
Column 12, lines 66-67, Eq. (6B)
Column 13, lines 6-7, Eq. (7)
Column 13, lines 43-44, Eq. (8)
Column 13, line 48, Eq. (9)
Column 13, lines 54-55, Eq. (10)

UNITED STATES PATENT AND TRADEMARK OFFICE
CERTIFICATE OF CORRECTION

PATENT NO. : 6,431,748 B1
DATED : August 13, 2002
INVENTOR(S) : Francis I. Baratta It is certified that error appears in the above-identified patent and that said Letters Patent is hereby corrected as shown below:

$$T(x,t) = QL/k \{ \alpha t/L^2 + (3x^2 - L^2)/6L^2 \\ - 2/\pi^2 \sum_{m=1}^{\infty} (-1)^m/m^2 \, [\exp(-\alpha m^2 \pi^2 t/L^2)] \cos(m\pi x/L) \} \quad (1)$$

$$T(t) = 2 T_0 \sum_{n=0}^{\infty} (-1)^n \{1 - erf[(2n+1)/2(\alpha t/L^2)^{1/2}]\} \quad (2)$$

$$T(t) = QL/k \{ \alpha t/L^2 - 1/6 \\ - 2/\pi^2 \sum_{m=1}^{\infty} (-1)^m/m^2 \, [\exp(-\alpha m^2 \pi^2 t/L^2)]\} \quad (1A)$$

$$T(t) = q/W \{ t/c - L^2 \rho/6k \\ - 2L^2 \rho/\pi^2 k \sum_{m=1}^{\infty} (-1)^m/m^2 \, [\exp(-\alpha m^2 \pi^2 t/L^2)]\} \quad (1B)$$

$$T(x,t) = QL/k \{ \alpha t/L^2 + 1/3 \\ - 2/\pi^2 \sum_{m=1}^{\infty} (-1)^m/m^2 \, [\exp(-\alpha m^2 \pi^2 t/L^2)] \cos(m\pi)\} \quad (1C)$$

$$dT/dt = Q/\rho c L \{ 1 + 2\sum_{m=1}^{\infty} (-1)^m \exp(-\alpha m^2 \pi^2 t/L^2) \cos(m\pi x/L)\} \quad (3)$$

$$dT/dt = T_0 L/(\pi \alpha t^3)^{1/2} \sum_{n=0}^{\infty} (-1)^n (2n+1) \exp[-(2n+1)^2/4\alpha t/L^2] \quad (4)$$

$$T(x,t) = Q/k \{1/h + x \\ - 2 \sum_{n=1}^{\infty} \exp(-\alpha \beta_n^2 t) \cos[(L-x)\beta_n](\beta_n^2 + h^2)/(\beta_n^2[h + L(\beta_n^2 + h^2)])\} \quad (6)$$

$$T(x,t) = Q/k \{1/h \\ - 2 \sum_{n=1}^{\infty} \exp(-\alpha \beta_n^2 t) \cos(L\beta_n) (\beta_n^2 + h^2)/(\beta_n^2[h + L(\beta_n^2 + h^2)])\} \quad (6A)$$

UNITED STATES PATENT AND TRADEMARK OFFICE
CERTIFICATE OF CORRECTION

PATENT NO. : 6,431,748 B1
DATED : August 13, 2002
INVENTOR(S) : Francis I. Baratta It is certified that error appears in the above-identified patent and that said Letters Patent is hereby corrected as shown below:

$$T(x,t) = Q/k \{1/h + L - 2\sum_{m=1}^{\infty} \exp(-\alpha\beta^2_n t)(\beta^2_n + h^2)/(\beta^2_n[h + L(\beta^2_n + h^2)])\} \quad (6B)$$

$$T = T_0 \{1/(1 + hL) - 2\sum_{m=1}^{\infty} \exp(-\alpha\gamma^2_n t) \sin(L\gamma_n)(\gamma_n^2 + h^2)/(\gamma_n[h + L(\gamma^2_n + h^2)])\} \quad (7)$$

$$dT/dt = 2Q/\rho c \sum_{m=1}^{\infty} \exp(-\alpha\beta^2_n t) \cos(L\beta_n)(\beta^2_n + h^2)/[h + L(\beta^2_n + h^2)], \quad (8)$$

$$dT/dt = 2Q/\rho c \sum_{m=1}^{\infty} \exp(-\alpha\beta^2_n t)(\beta^2_n + h^2)/[h + L(\beta^2_n + h^2)] \quad (9)$$

$$dT/dt = 2 T_0 \alpha \sum_{m=1}^{\infty} \gamma_n \exp(-\alpha\gamma^2_n t) \sin(L\gamma_n)(\gamma_n^2 + h^2)/[h + L(\gamma^2_n + h^2)] \quad (10)$$

Signed and Sealed this

Twenty-sixth Day of August, 2003

JAMES E. ROGAN
*Director of the United States Patent and Trademark Office*